United States Patent
Noack et al.

[11] Patent Number: 6,128,536
[45] Date of Patent: Oct. 3, 2000

[54] THERAPY APPARATUS FOR THE FUNCTIONAL ELECTROMYOSTIMULATION OF SMOOTH MUSCLE CELLS

[75] Inventors: Thomas Noack, Kirchhain; Christian Stief, Hemmingen; Edgar Weller, Dresden, all of Germany

[73] Assignee: Medizintechnik Dipl.-Ing. Heise Vertriebs GmbH, Dortmund, Germany

[21] Appl. No.: 08/913,924

[22] PCT Filed: Mar. 12, 1996

[86] PCT No.: PCT/EP96/01043

§ 371 Date: Oct. 27, 1997

§ 102(e) Date: Oct. 27, 1997

[87] PCT Pub. No.: WO96/28211

PCT Pub. Date: Sep. 19, 1996

[30] Foreign Application Priority Data

Mar. 13, 1995 [DE] Germany ............... 195 08 591

[51] Int. Cl.[7] ........................................ A61N 1/00
[52] U.S. Cl. .................................. 607/39; 607/143
[58] Field of Search ......................... 607/39–41, 59, 607/72, 138, 143

[56] References Cited

U.S. PATENT DOCUMENTS

| | | |
|---|---|---|
| 3,236,240 | 2/1966 | Bradeley . |
| 3,941,136 | 3/1976 | Bucalo . |
| 4,279,256 | 7/1981 | Bucalo . |
| 4,585,005 | 4/1986 | Lue et al. . |
| 4,664,100 | 5/1987 | Rudloff ............... 600/40 |
| 4,742,833 | 5/1988 | Barson ............... 607/143 |
| 4,881,526 | 11/1989 | Johnson et al. . |
| 5,441,528 | 8/1995 | Chang et al. ............. 607/69 |
| 5,571,118 | 11/1996 | Boutos ................ 607/138 |

FOREIGN PATENT DOCUMENTS

| | | |
|---|---|---|
| 2541119 | 8/1984 | France . |
| 3827232 | 11/1989 | Germany . |
| 2278547 | 12/1994 | United Kingdom . |
| 8402465 | 7/1984 | WIPO . |

OTHER PUBLICATIONS

H. Edel: "Fibel der elektrodiagnostik und elektrotherapie" 1977, Verlag Theodor Steinkopf, Dresden XP002003053, p. 142–145.

*Primary Examiner*—Jeffrey R. Jastrzab
*Attorney, Agent, or Firm*—Horst M. Kasper

[57] ABSTRACT

A method is disclosed for treating erectile dysfunction includes arranging a therapy apparatus to be connected to an electrical power source, placing a skin electrode on two sides laterally of a penile shaft and employing an amplifier for performing the stimulation. A current is applied transcutaneously for a regeneration of the smooth musculature of the penile corpus carnaversum. The current applied has zero line-symmetrical impulses of rectangular or trapezoid form with a built-up time of 0,01 to 2 seconds, a stimulation period of 1 to 60 seconds direct or alternating, a stimulation pause of 0.01 to 60 seconds, a frequency range of 1 to 50 Hertz and an impulse period of 100 $\mu$s to 10 ms. Advantageously, the stimulation is performed diagonally alternatingly with zero-line symmetric impulses of trapezoidal shape in a first channel and in a second channel with alternating stimulations. The frequency for the first channel is 10 to 20 Hertz and the frequency for the second channel is 20 to 35 Hertz. The impulse duration is from about 100 to 150 $\mu$s. The rise time is 0.5 seconds, the stimulation time is 5 seconds per channel, and the pause between stimulations is 0.5 seconds. The current is increased until a sensory perception of current is reported.

19 Claims, 3 Drawing Sheets

THERAPY APPARATUS FOR THE FUNCTIONAL ELECTROMYOSTIMULATION OF SMOOTH MUSCLE CELLS

BACKGROUND OF THE INVENTION

1. Field of the Invention

The invention concerns a therapy apparatus for the functional electromyostimulation of smooth muscle cells, especially of the penis and of the urethra and their connective tissue within the human body by meens of which a regeneration of the smooth muscles and thus a functional improvement of the diseased cell connective tissues and organs is achievable.

2. Brief Description of the Background of the Invention Including Prior Art

In the case of the incidence of e.g. 3 to 4 million men in Germany with chronic erectile dysfunction, there is a great medicinal importance for the principally possible therapeutic options. At the present point of time, the corpus cavernosum autoinjection therapy (CCAT; 1–5), the penis prosthesis implantation (6–8) or the use of a vacuum system form the cornerstones of the therapy of organogenic erectile dysfunction.

However, because of the absence of spontaneity, of possible side effects or af the non-physiological manner of working, many patients refuse these treatment alternatives from the onset, Furthermore, high drop-out rates or a considerable number of dissatisified users are to be ascertained in the long-term observation (5). As alternative, for these patients there is only available the reconstructive penile blood vessel surgery (9, 10) which, however, only comes into question for selected patients because of the complex aetiology of the erectile dysfunction.

In recent electron microscopic studies, it could be shown that, in the case of many patients, a degeneration of the cavernous smooth muscles is present as cause of the erectile dysfunction (11–13). In the case of these patients, as therapy possibilities only the prosthetic provision of the vecuum aid comes into question. Possibilities of the regeneration of these cavernous smooth muscle cells which make possible substantially more therapeutic options for the affected patients are, however, hitherto not known.

In the case of patients in the case of which, because of a temporary inactivation of the skeletal musculature, e.g. by application of a plaster in the case of fractures, or of the temporary lesion of muscle-innervating nerves after accidents or operations, it results in an atrophy of the musculature with the known disadvantageous results, for the evoidance of this atrophy during the resting or lesion phase, transcutaneous stimulation current can be applied. This process represents a standard method (14–17) in the treatment or prophylaxis of atrophies of the skeletal or striated musculature.

Because of the poor accessibility of the organs consisting of smooth muscle cells (e.g. oesophagus, uterus, urethra, urinary bladder), the thereby poor delimitation from other organs and the fundamentally different stimulation of the smooth muscle cells in contradistinction to striated muscle cells, no possibilities exist to influence these organs by means of transcutaneously applied current.

SUMMARY OF THE INVENTION

1. Purposes of the Invention

It is an object of the present invention to provide treatments of disturbances, such as for example of certain forms of erectile dysfunction or incontinence.

It is another object of the present invention to provide treatments promising a regeneration of the cavernous smooth muscles.

These and other objects and advantages of the present invention will become evident from the description which follows.

2. Brief Description of the Invention

The present invention provides treatments of disturbances, such as for example certain forms of erectile dysfunction or incontinence, which are thereby possible and which otherwise cannot be achieved with the apparatus and aids presently available.

Our own hitherto unpublished investigations on isolated corpus cavernosum tissue have, surprisingly, now shown that the smooth musculature of the penile corpus cavernosum has a phase electrical activity of about 20 hz.

Furthermore, our own hitherto unpublished investigations on patients with erectile dysfunction showed that, in the case of many of these patients, a partial denervation of the penile corpus cavernosum is present as cause of the erectile disturbance.

This surprisingly, completely new and unexpected knowledge now justifies the use of transcutaneously applied current for the regeneration of the smooth musculature of the penile corpus cavernosum as treetment possibilities of the erectile dysfunction.

An inventive stipulation for the feasibility of such therapies is the arranging of the therapy apparatus in such a way that it is battery-, accummulator- or mains-operated and that the arrangement of the stimulation takes place in such a way that via, in each case, one or more skin electrodes on both sides laterally of the penile shaft, the stimulation can take place directly via a one- or two-channel amplifier or via the small of the back.

A further inventive stipulation for the feasibility of such therapies in the arranging of the therapy apparatus in such a way that the arranging of the stimulation parameters takes place in such a manner that it permits zero line-symmetrical impulses of rectangular or trapezium form with a build-up time of 0,01 to 2 seconds, a stimulation period of 1 to 60 seconds direct or alternating, a stimulation pause of 0,01 to 60 seconds, a frequency range of 1 to 50 Hertz and an impulse period of 100 $\mu$s to 10 ms or a specifically defined subgroup of the above-mentioned parameters.

The stimulation of the muscle cells takes place via surface electrodes which can be usable one or more times or via needle- or intraurethrally-applicable electrodes usable one or more times.

Furthermore, the possibility exists to store and afterwards to retrieve the treatment times and the employed parameters by storage possibilities within or outside of the device.

The novel features which are considered as characteristic for the invention are set forth in the appended claims. The invention itself, however, both as to its construction and its method of operation, together with additional objects and advantages thereof, will be best understood from the following description of specific embodiments when read in connection with the accompanying drawing.

BRIEF DESCRIPTION OF THE DRAWING

In the accompanying drawing, in which are shown several of the various possible embodiments of the present invention.

DESCRIPTION OF INVENTION AND PREFERRED EMBODIMENT

Figure 1:
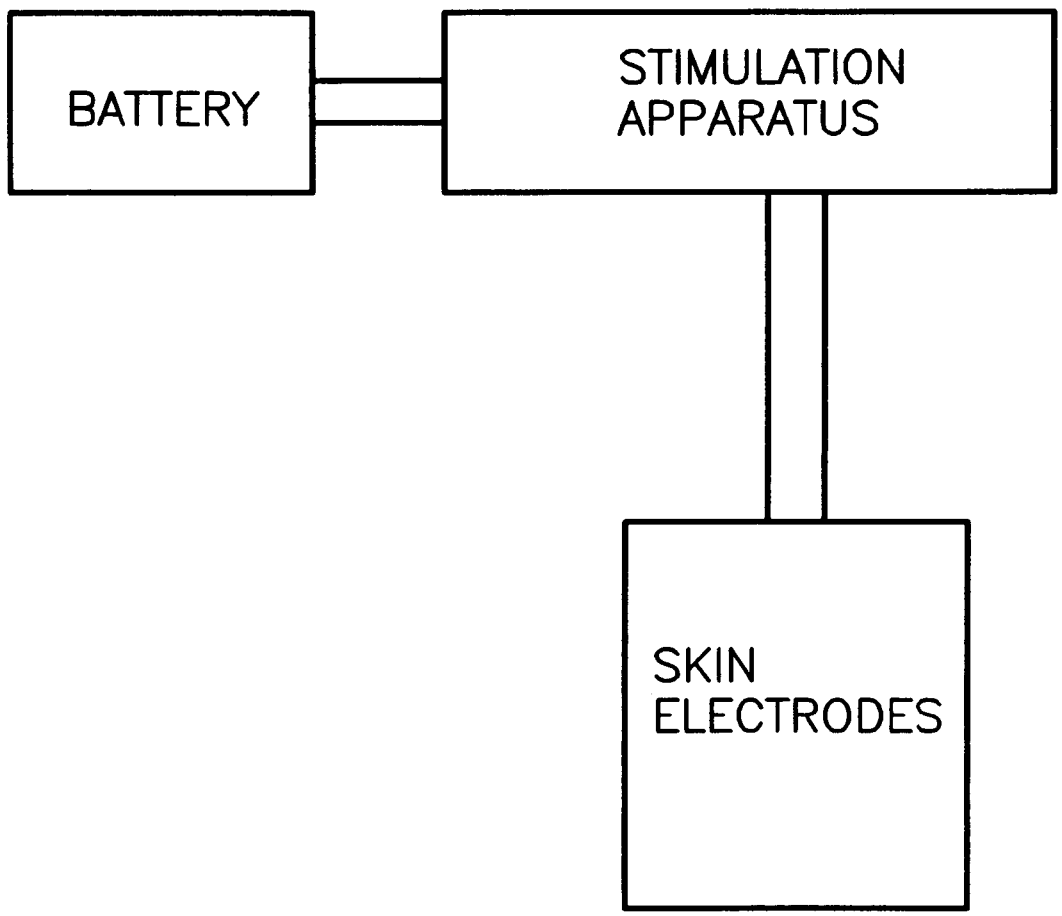
FIG. 1 is a view showing a simplified schematic diagram of an apparatus according to the present invention.

The general construction of an apparatus employed in accordance with the present invention is illustrated in FIG. 1 with a power supply furnished by a battery electrically connected to a stimulation apparatus and then skin electrodes also electrically connected to the stimulation apparatus.

Figure 2:
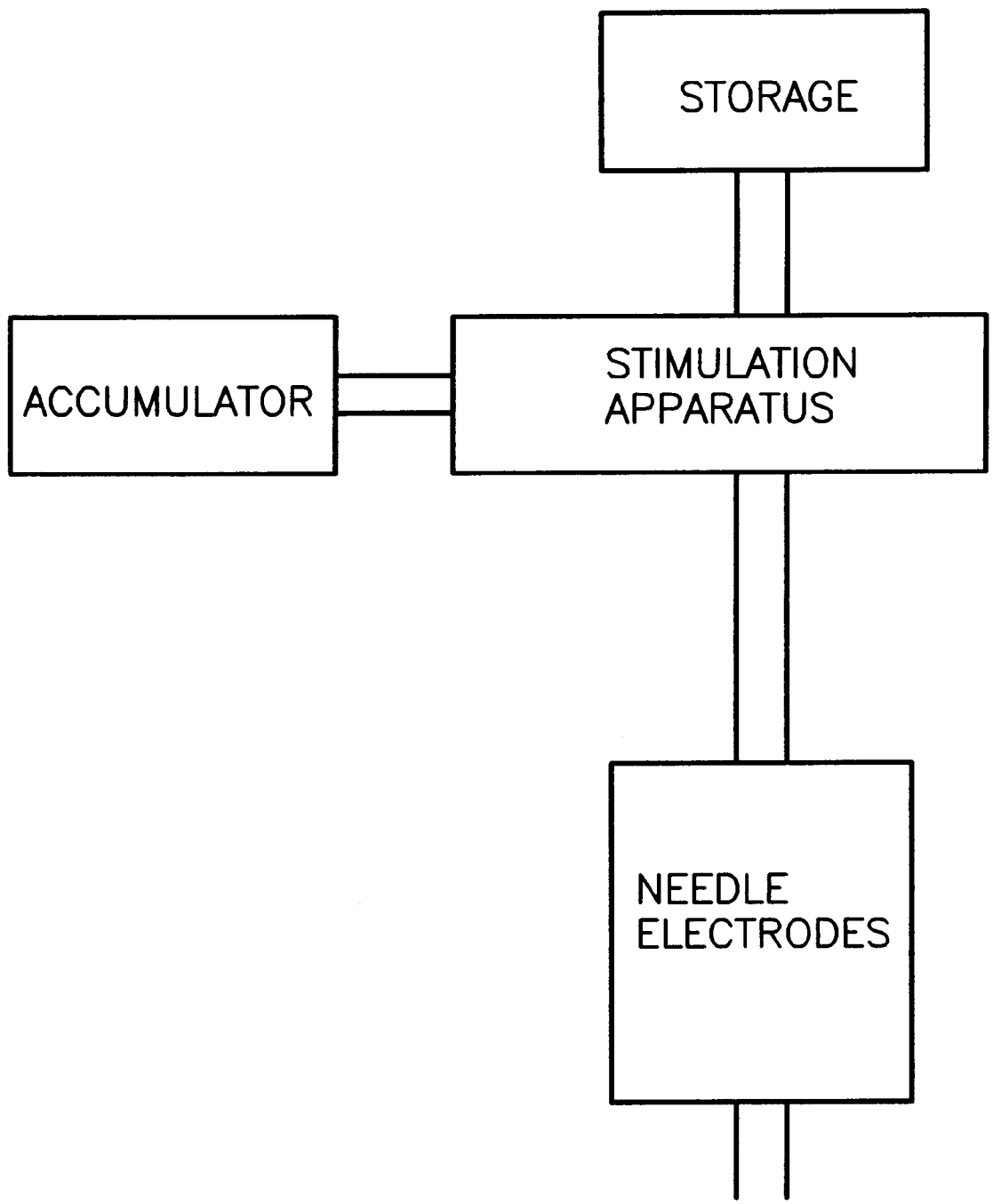
FIG. 2 is a view showing a schematic diagram similar to the diagram of FIG. 1, however including the feature of memory storage of treatment parameters and treatment data.

FIG. 2 shows a diagem similar to that of FIG. 1, however needle electrodes are employed and furthermore a memory storage is connected to the stimulation apparatus for storing and retrieving treatment parameters and treatment data.

Figure 3:
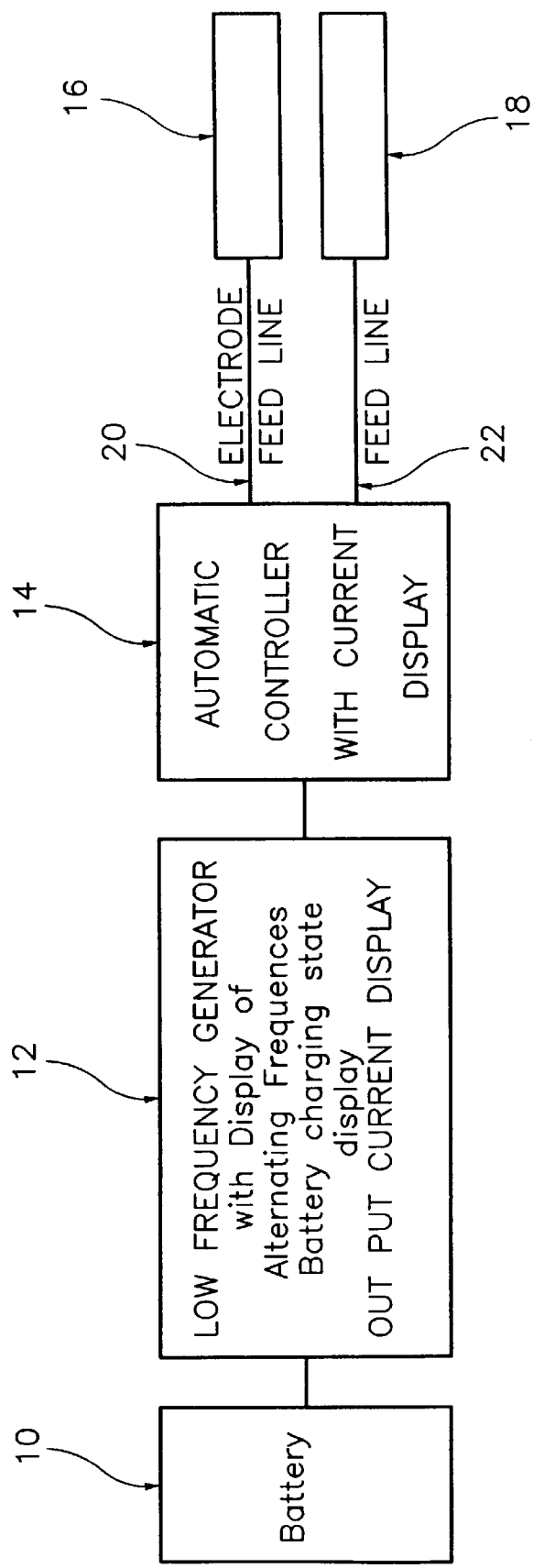
FIG. 3 is a view showing a schematic diagram of a preferred embodiment.

FIG. 3 again employs a battery 10 for furnishing electrical power. The battery 10 is connected a low frequency generator 12 including a display of the alternating current frequency, of the charge state of the battery and of the output current. An automatic controller 14 is electrically connected to the low frequency generator 12. a current display is furnished on the automatic controller. Electrodes 16 and 18 are electrically connected to the automatic controller 14.

The results of such therapy procedures with the therapy apparatus according to the invention are shown in the following:

The therapy apparatus according to the invention was used on 22 patients with erectile dysfunction in which otherwise no reconstructive therapy procedures have produced success. All patients were sworn to secrecy with regard to this treatment process.

A satisfactory therapy result could be achieved in the case of 8 of these 22 patients.

The following Tables give exact information regarding the patient groups, which were broken down according to the treatment success:

TABLE 1

Patients after FEMCC and completely spontaneous erection after FEMCC

| name | anamnesis | CC-EMG | Doppler | MF |
|---|---|---|---|---|
| R.P. | prolaps L4/5 | n | p | 60 |
| K.S. | hypertension | n | n | 150 |
| W.B. | — | n | n | 10 |
| S.M. | failure anxiety | n | n | — |
| R.S. | diabetes I, time after Hauri op | n | p | 8 | n = normal
p = pathological
MF = maintenance flow in ml/minute measured during the pharmacocavernosometry

TABLE 2

Patients after FEMCC and and positive CCAT-Test after FEMCC

| name | anamesis | CC-EMG | Doppler | MF |
|---|---|---|---|---|
| H.B. | ped | n | p | 10 |
| T.B. | — | p | n | 40 |
| G.M. | diabetes I | p | p | 10 | n = normal
p = pathological

TABLE 2-continued

Patients after FEMCC and and positive CCAT-Test after FEMCC

| name | anamesis | CC-EMG | Doppler | MF |
|---|---|---|---|---|

MF = maintenance flow in ml/minute measured during the pharmacocavernosometry
ped = primary erectile dysfunction

TABLE 3

Failure on FEMCC

| name | anamesis | CC-EMG | Doppler | MF |
|---|---|---|---|---|
| E.M. | — | p | p | 60 |
| H.N. | 2 × A.I. pelv. # | n | n | 60 |
| W.L. | DM II, MI, AA | p | p | 80 |
| A.E. | pelv. # | p | n | not done |
| H.L. | ped, VA, AR, VL | n | n | 8 |
| G.S. | DM I, VL | p | p | 80/7 |
| D.G. | AR | p | p | 4 |
| B.W. | A.I. NTx | n | p | 200 |
| K.A. | ALL | p | n | 38 |
| D.N. | DM II, Hyp | p | n | 20 |
| R.H. | ped | p | p | 80 |
| K.K. | VL | n | n | 45/30 |
| E.R. | ped | p | n | 50 |
| M.P. | dialysis | p | n | 80 | ped = primary erectile dysfunction
A.I. = apoplexy
pelv. # = pelvis fracture with urethral avulsion
DM = diabetes mellitus
MI = infarct
AA = absolute arrhythmia
VA = failure anxiety
AR = post-penile arterialisation
VL = post-penile vein surgery
ALL = acute lymphatic leukaemia
Hyp = hypertension
n = normal
p = pathological
MF = maintenance flow Therefore, the therapy apparatus according to the invention consists of needle or surface electrodes, a mobile or stationary apparatus for the stimulation of smooth muscle cells with stimulation possibilities which permits zero line-symmterical impulses of rectangular or trapezium form with a build-up time of 0.01 to 2 seconds, a stimulation period of 1 to 60 seconds direct or alternating, a stimulation pause of 0.01 to 60 seconds, a frequency range of 1 to 50 Hertz and an impulse period of 100 $\mu$s to 10 ms or a specifically defined sub-group of the above-mentioned parameters.

Some additional aspects and possibilities in accordance with the invention are as follows.

In one exemplary methodology, patients with chronic erectile dysfunction may receive daily (3 to 5 times; 20 min per event) transcutaneous functional electromyostimulation of the corpus cavernosum smooth muscles ("FEMCC"): for example, zero-line symmetric impulses of trapezoid shape, 2-channel device with alternating stimulations; frequency (f), 10–20 Hz for channel 1 and 20–35 Hz for channel II; impulse duration ($t_1$), 100–150 $\mu$s; approx. 12 mA; rise time, 0.5 s; stimulation time, 5 s/channel; pause between stimulations 0.5 s. Responsive patients might either regain full spontaneous erections or become responsive to vasoactive drugs after FEMCC.

One main aspect of the invention is to utilize the effect of transcutaneaus functional electromyostimulation of the corpus cavernosum smooth muscles (FEMCC) in patients with erectile dysfunction.

All patients are preferably subjected to a comprehensive approach regarding the etiology of their erectile dysfunction.

This approach includes a case history, physical examination, blood laboratory workup, sexual case history (done by a psychiatrist), corpus cavernosum electromyography (CC-EMG) pharmacotesting, and Doppler. When indicated patients may be subject to further examinations such as cavernosometry and cavernosography, penile angiography, or somaromotoric and/or autonomic neurological examinations.

In the case of patients who do not respond to maximal doses of intracavernous injections (30 mg papaverine plus 1 mg phentolamine) plus additional psychogenic or reflexogenic stimulation they are considered as having a high likelihood of venous leakage as a (co)factor for their erectile dysfunction. Since CC-EMG has been found to be an important prognostic factor for penile venous surgery, only those patients who fail to respond to vasoactive drugs and who do not have a normal CC-EMG finding are appropriate candidates to undergo cavernosometry and cavernosography and, possibly, venous surgery. Nonresponders with abnormal CC-EMG findings will most likely have autonomic neuropathy and/or cavernous smooth-muscle degeneration and are therefore unsuitable candidates for reconstructive surgery. For these patients other therapeutic strategies are advised, such as vacuum devices, penile prosthesis, or a trial with intracavernous injection of a combination af calcitonin-gene-related peptide (CGRP) plus prostaglandin E1 (PGE1).

Nonresponders with abnormal CC-EMG findings as well as patients who were unwilling to accept other treatment options are favorable candidates for FEMCC as an alternative treatment for their erectile dysfunction.

The electrodes are placed preferably with two electrodes placed bilaterally over the penile shaft and connected in such a way that a diagonal current is achieved. Four electrodes are preferably connected to a battery-operated stimulator (two channels) designed for diagonal alternating stimulation and the stimulation parameters are established (for example: zero-line symmetric impulses of trapezoid shape; two-channel device with alternating stimulations; rise time 0.5 s; stimulation time; 5 s; pause between stimulations, 0.5 s). The frequency may be modified individually according to the patient's perception (ranges freqency (f), 10–20 Hz for channel I and 20–35 Hz for channel II; impulse duration ($t_1$), 100–150 $\mu$s) until a sensory perception of current (approximately 12 mA is reported. Patients preferably undergo stimulation three to five times daily, with each treatment session lasting for at least 20 minutes.

There may be a slight chance of a placebo effect whenever daily treatment sessions are conducted over a longer period. Nonetheless, most of the therapeutic effect observed after FEMCC is thought to be due to a regeneration of the cavernous smooth-muscles.

In the treatment of smooth-muscle denervation and subsequent smooth-muscle atrophy transcutaneous application of low-Frequency electric current has not been used, to the best af our knowledge. Although erectile dysfunction is a multifactorial event, with many psychic and organic factors playing an imporcant role, the intactness of the cavernous smooth-muscle cells is a key requisite for the erectile process. The regeneration of the cavernous smooth-muscle cells induced by transcutaneous applications of low-frequency electric current should result either in a regain of spontaneous erectile capacity, if no other factor is involved in the etiology of the erectile dysfunction, or in a response to the intracavernous injection of vasoactive drugs if other factors, e.g. autonomic neuropathy, are involved.

The parameters of the electric current applied in the present study are based on both experimental findings and deductions from the therapy of striated muscles. A frequency range of 10–35 Hz is preferred since these frequencies are thought to induce the best erectile response when direct neurostimulation is applied to the cavernous nerve.

Different frequency ranges for channels I and II were chosen in accordance with experiences in striated muscle rehabilitation, where different frequencies stimulate different groups of muscle cells, thus resulting in a better overall response. An impulse duration of 100–150 $\mu$s was preferable since such an impulse width does not typically provoke pain or discomfort.

The parameters described herein will stimulate regeneration only of cavernous tissue with intact or partially intact autonomic supply. The electric current generated as described will induce a discharge of synaptic information, resulting in ("indirect") changes in the cavernous smooth-muscle regeneration. Such circumstances may explain a relatively low success rate (of 33%) with some patients. For the possible achievement of higher rates of success, direct electrical stimulation of the cavernous smooth-muscle cells is an approach, for example using different stimulation parameters of f, 1–5 Hz; $t_1$, 1–10 ms.

In general, FEMCC is feasible and results in an improvement in erectile capacity in a significant number of patients.

It will be understood that each of the elements described above, or two or more together, may also find a useful application in other types of penile treatment configurations and muscle stimulating procedures differing from the types described above.

While the invention has been illustrated and described as embodied in the context of a therapy apparatus for the functional electromyostimulation of smooth muscle cells, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it f or various applications without omitting features that, from the standpoint of prior art, fairly constitute essential characteristics of the generic or specific aspects of this invention.

What is claimed as new and desired to be protected by Letters Patent is set forth in the appended claims.

List of Citations (1) Virag R. (1982) Intracavernous injection of papaverine for erectile failure. Letter to the editor. Lancet 2: 938

(2) Brindley G. S. (1983) Cavernosal alpha-blockade: a new technique for investigating and treeting erectile dysfunction. Brit. J. Psychiatr. 143: 332–337

(3) Zorgniotti A. W. and Lefleur R. S. (1985) Autoinjection of the corpus cavernosum with a vasoactive drug combination for vasculogenic impotence. J. Urol. 133: 39–43

(4) Ishii N., Watanabe H., Irisawa C. (1989) Intracavernous injection of prostaglandin El for the treatment of erectile impotence. J. Urol. 141: 323–327

(5) Junemann K. P. and Alken P. (1989) Pharmacotherapy of erectile dysfunction. Int. J. Impotence Res. 1: 71–85

(6) Scott F. B., Bradley W. E., Timm G. W. (1973) Management of erectile impotence. Urology 2: 80–85

(7) Small M. P., Carrion H. M., Gordon J. A. (1975) Small-Carrion penile prosthesis, Urology 5: 479–484

(8) Montague D. K. (1989) Penile prosthesis. An overview. Urol. Clin. N. Amer. 16: 7–17

(9) Levine F. J., Gasior B. L., Goldstein I. (1989) Reconstructive arterial surgery for impotence. Sem. Interven. Radiol. 6: 220–229

(10) Goldstein I. (1987) Penile revascularisation. Urol. Clin. N. Amer. 14: 805–812

(11) Persson C., Diedrichs W., Lue T. F., Yen T. S., Fishman I., Mc. Lin P. H., Tanagho E. T. (1985) Correlation of altered ultrastructure with clinical arterial evaluation. J. Urol. 142: 1462–1467

(12) Wetterauer U., Stief C. G., Kulvelis F., Staubesand, Sommerkamp H. (1990) The electron microscope ultrastructure of cavernous tissue in erectile dysfunction. J. Urol. 143: 509A

(13) Mersdorf A., Goldsmith P., Diederichs W., Padula C., Lue T. F., Fishman I., Tanagho E. T, (1991) Ultrastructural changes in impotent penile tissue. J. Urol. 145: 749–754

(14); Edel H. (1977) Fibel der Elektrodiagnostik und Elektrotherapie, Verlag Theodor Steinkopf, Dresden

(15) Taylor P. N., Ewins D. J., Fox B., Grundy D., Swain I. D. (1993) Limb blood flow, cardiac output and quadriceps muscle bulk following spinal cord injury and the effect of training for the Odstock functional electrical stimulation standing system. Paraplegia 31: 303–309

(16) Trimble M. H., Enoka R. M. (1991) Mechanisms underlying the training effects associated with neuromuscular electrical stimulation. Phys. Ther. 71: 273–281

(17) Delitto A., Snyder-Mackler L. (1990) Two theories of muscle strength augmentation using percutaneous electrical stimulation. Phys. Ther. 70: 158–165

We claim:

1. A therapy apparatus for the electrical stimulation of smooth muscle cells comprising means for stimulating the smooth musculature of the penile corpus cavernosum, said means comprising electrodes connected to an electrical power source;

means for applying zero line-symmetrical impulses of rectangular or trapezoid form with a built-up time of 0.01 to 2 seconds, a stimulation period of 1 to 60 seconds direct or alternating, a stimulation pause of 0.01 to 60 seconds, a frequency range of 1 to 50 Hertz and an impulse period of 100 $\mu$s to 10 ms.

2. The therapy apparatus according to claim 1 wherein the electrodes are skin electrodes to be disposed on both sides laterally of the penile shaft, further comprising an amplifier connected to the electrodes and to the power source.

3. The therapy apparatus according to claim 1 wherein the electrodes are a member selected from the group consisting of surface electrodes, needle-electrodes, and intraurethrally-applicable electrodes.

4. The therapy apparatus according to claims 2 to 1 further comprising memory storage means for storing the treatment times and the parameters used within or outside of the apparatus and these are afterwards retrievable.

5. A method for treating erectile dysfunction comprising arranging a therapy apparatus to be connected to an electrical power source;

placing a skin electrode on two sides laterally of a penile shaft;

employing an amplifier for performing the stimulation;

applying zero line-symmetrical impulses of rectangular or trapezoid form with a built-up time of 0.01 to 2 seconds, a stimulation period of 1 to 60 seconds direct or alternating, a stimulation pause of 0.01 to 60 seconds, a frequency range of 1 to 50 Hertz and an impulse period of 100 $\mu$s to 10 ms.

6. The method for treating erectile dysfunction according to claim 5 further comprising applying current transcutaneously for a regeneration of the smooth musculature of the penile corpus cavernosum.

7. The method for treating erectile dysfunction according to claim 5 further comprising stimulating muscle cells with an electrode, which is a member selected from the group consisting of surface electrodes, needle-electrodes, and intraurethrally-applicable electrodes.

8. A method for treating erectile dysfunction comprising arranging a therapy apparatus to be connected to an electrical power source;

placing a skin electrode on two sides laterally of a penile shaft;

employing an amplifier for performing stimulation;

furnishing daily transcutaneous functional electromyostimulation of the corpus cavernosum smooth muscles with zero-line symmetric impulses of trapezoidal shape in a first channel and in a second channel with alternating stimulations, wherein the frequency for the first channel is 10 to 20 Hertz and wherein the frequency for the second channel is 20 to 35 Hertz, wherein the impulse duration is from about 100 to 150 $\mu$s, wherein the current is about 12 milliamperes, wherein the rise time is 0.5 seconds, wherein the stimulation time is 5 seconds per channel, wherein the pause between stimulations is 0.5 seconds.

9. The method for treating erectile dysfunction according to claim 8 further comprising applying current transcutaneously for a regeneration of the smooth musculature of the penile corpus cavernosum.

10. The method for treating erectile dysfunction according to claim 8 further comprising stimulating muscle cells with an electrode, which is a member selected from the group consisting of surface electrodes, needle-electrodes, and intraurethrally-applicable electrodes.

11. A method for treating erectile dysfunction comprising arranging a therapy apparatus to be connected to an electrical power source;

placing a skin electrode on two sides laterally of a penile shaft;

employing an amplifier for performing stimulation;

placing two electrodes bilaterally over a penile shaft;

connecting the two electrodes in such a way as to achieve a diagonal current connecting four electrodes to a battery operated stimulator;

diagonally alternatingly stimulating with zero-line symmetric impulses of trapezoidal shape in a first channel and in a second channel with alternating stimulations, wherein the frequency for the first channel is 10 to 20 Hertz and wherein the frequency for the second channel is 20 to 35 Hertz, wherein the impulse duration is from about 100 to 150 $\mu$s, wherein the rise time is 0.5 seconds, wherein the stimulation time is 5 seconds per channel, wherein the pause between stimulations is 0.5 seconds;

increasing the current until a sensory perception of current is reported.

12. The method for treating erectile dysfunction according to claim 11 further comprising applying current transcutaneously for a regeneration of the smooth musculature of the penile corpus cavernosum.

13. The method for treating erectile dysfunction according to claim 11 further comprising stimulating muscle cells with an electrode, which is a member selected from the group consisting of surface electrodes, needle-electrodes, and intraurethrally-applicable electrodes.

14. A method for treating erectile dysfunction comprising arranging a therapy apparatus to be connected to an electrical power source;

placing a skin electrode on two sides laterally of a penile shaft;

employing an amplifier for performing stimulation;

furnishing repeated transcutaneous functional electromyostimulation of the corpus cavernosum smooth muscles with zero-line symmetric impulses of trapezoidal shape in a first channel and in a second channel with alternating stimulations, wherein the frequency for the first channel is 10 to 20 Hertz and wherein the frequency for the second channel is 20 to 35 Hertz, wherein the impulse duration is from about 100 to 150 $\mu$s, wherein the rise time is 0.5 seconds, wherein the stimulation time is 5 seconds per channel, wherein the pause between stimulations is 0.5 seconds.

15. The method for treating erectile dysfunction according to claim 14 further comprising applying current transcutaneously for a regeneration of the smooth musculature of the penile corpus carnaversum.

16. The method for treating erectile dysfunction according to claim 14 further comprising stimulating muscle cells with an electrode, which is a member selected from the group consisting of surface electrodes, needle-electrodes, and intraurethrally-applicable electrodes.

17. A method for treating erectile dysfunction comprising arranging a therapy apparatus to be connected to an electrical power source;

placing a skin electrode on two sides laterally of a penile shaft;

employing an amplifier for performing stimulation;

furnishing repeated transcutaneous functional electromyostimulation of the corpus cavernosum smooth muscles with zero-line symmetric impulses of trapezoidal shape with a build-up time of 0.01 to 2 seconds, a stimulation period of 1 to 60 seconds, a stimulation pause of 0.01 to 60 seconds, a frequency range of from about 1 to 50 Hertz and an impulse period of 100 $\mu$s to 10 ms.

18. The method for treating erectile dysfunction according to claim 17 further comprising applying current transcutaneously for a regeneration of the smooth musculature of the penile corpus cavernosum.

19. The method for treating erectile dysfunction according to claim 17 further comprising stimulating muscle cells with an electrode, which is a member selected from the group consisting of surface electrodes, needle-electrodes, and intraurethrally-applicable electrodes.

* * * * *